US00PP09933P

United States Patent [19]

Fuess

[11] Patent Number: Plant 9,933

[45] Date of Patent: Jun. 24, 1997

[54] CHRYSANTHEMUM PLANT NAMED 'EMPIRE SPOTLIGHT'

[76] Inventor: Janet S. Fuess, 22 Country Club Dr., New York Mills, N.Y. 13417

[21] Appl. No.: 616,645

[22] Filed: Mar. 15, 1996

[51] Int. Cl.[6] ..... A01H 5/00

[52] U.S. Cl. ..... Plt./76

[58] Field of Search ..... Plt./74.1, 80, 76

*Primary Examiner*—Howard J. Locker

*Attorney, Agent, or Firm*—Foley & Lardner

[57] ABSTRACT

A Chrysanthemum plant named Empire Spotlight particularly characterized by its flat capitulum form; decorative capitulum type; pink overlaid white floret color; diameter across face of capitulum of 67 to 76 mm when fully opened; branching pattern is spreading, with 6 to 8 laterals developing after pinch when grown outside under natural daylength in fall flowerings; natural season flower date of August 14 to 27 when planting rooted cuttings on June 17 to 18 in Salinas, Calif., and of Sepember 22 to 30 when planting rooted cuttings June 15 to 22 in Hightstown, N.J.; plant height of 28 to 33 cm when grown in fall under natural daylength with no growth regulators; and durable, uniform performance.

3 Drawing Sheets

The present invention comprises a new and distinct cultivar of Chrysanthemum, botanically know as *Dendranthema grandiflora,* and referred to by the cultivar name Empire Spotlight.

Empire Spotlight, identified as 9801 (A91-4), was oiginated from a cross made by Janet S. Fuess in a controlled breeding program in New Hartford, N.Y. in October 1990.

The female parent of Empire Spotlight was an unnamed seedling, identified as F88-2, and described as a purple decorative garden mum.

The male parent of Empire Spotlight was an unnamed seedling, identified as F89-6, and described as a pink decorative garden mum.

Empire Spotlight was discovered and selected as one flowering plant within the progeny of the stated cross by Janet S. Fuess in August of 1991 in New Hartford, N.Y.

The first act of asexual reproduction of Empire Spotlight was accomplished when vegetative cuttings were taken from the initial selection in October of 1991 in a controlled environment in New Hartford, N.Y. by Janet S. Fuess.

Horticultural examination of controlled flowerings of successive plantings has shown that unique combination of characteristics as herein disclosed for Empire spotlight are firmly fixed and are retained through successive generations of asexual reproduction.

Empire Spotlight has not been observed under all possible environmental conditions, The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Empire Spotlight, which, in combination, distinguish this Chrysanthemum as a new and distinct cultivar:

1. Flat capitulum form.
2. Decorative capitulum type.
3. Pink overlaid white floret color.
4. Diameter across face of capitulum of 67 to 76 mm when fully opened.
5. Branching pattern is spreading, with 6 to 8 laterals developing after pinch when grown outside under natural daylength in fall flowerings.

6. Natural season flower date of August 14 to 27 when planting rooted cuttings on June 17 to 18 in Salinas, Calif., and of September 22 to 30 when planting rooted cuttings June 15 to 22 in Hightstown, N.J.
7. Plant height of 28 to 33 cm when grown in fall under natural daylength with no growth regulators.
8. Durable, uniform performance.

The accompanying photographic drawings show typical inflorescence and leaf characeristics of Empire Spotlight, with the colors being as nearly true as possible with illustrations of this type.

Sheet 1 is a color photograph of Empire Spotlight grown in natural season outside conditions in Salinas, Calif.

Sheet 2 is a black and white photograph of three views of the inflorescence of Empire Spotlight.

Sheet 3 is a black and white photograph showing the upper and under sides of the leaves of Empire spotlight at 3 stages of development (mature, intermediate and immature). In sheets 2 and 3 a measuring tape in centimeters has been added.

Of the commercial cultivars known to the inventor, the most similar in comparision to Empire Spotlight is the cultivar identified as Sophia, disclosed in U.S. Pat. No. P.P. 9,558. Reference is made to attached Chart A, which compares certain characteristics of Empire Spotlight to the same characteristics of Sophia.

Similar traits are capitulum form and type, and branching pattern. The flowering response under natural season fall flowering conditions is comparable for both cultivars, The ray floret color of Empire Spotlight is pink-overlaid white, while the ray floret color of Sophia is described as light purple. Empire Spotlight has a larger diameter of capitulum, and a taller plant height when compared with Sophia.

In the following description color references are made to The Royal Horticultural Society Colour Chart. The color values were determined on plant material grown as a pinched garden mum grown outdoors in Salinas, Calif. on Aug. 18, 1995.

Classification:

*Botanical.*—*Dendranthema grandiflora* cv Empire Spotlight.

*Commmercial.*—Flat decorative garden mum.

INFLORESCENCE

A. Capitulum:

*Form.*—Flat

*Type.*—Decorative.

*Diameter across face.*—67 to 76 mm when fully opened.

B. Corolla of ray florets:

*Color (general tonality from a distance of three meters)* .—Pink-overlaid white.

*Color (upper surface).*—White, overlaid with 70D.

*Color (under surface).*—White, overlaid with 70D.

*Shape.*—Longitudinal axis straight, cross section convex, dentate ray floret tip.

C. Corolla of disc florets:

*Color (mature).*—4A.

*Color (immature.*—144B.

D. Reproductive organs:

*Androecium.*—Present on disc florets only; no pollen.

*Gynoecium.*—Present on both ray and disc florets.

PLANT

A. General appearance:

*Height.*—28 to 33 cm when grown in fall under natural daylength with no growth regulators.

*Branching pattern.*—Spreading.

B. Foliage:

*Color (upper surface).*—147A.

*Color (under surface).*—147B.

*Shape.*—Lobed and slightly serrated.

CHART A

COMPARISONS MADE OF PLANTS GROWN UNDER NATURAL SEASON OUTDOOR CONDITIONS IN SALINAS, CALIFORNIA AND IN HIGHTSTOWN, NEW JERSEY

| CULTIVAR | EMPIRE SPOTLIGHT | SOPHIA |
|---|---|---|
| Ray floret color | Pink overlaid white, pink center | Light purple |
| Capitulum form and type | Flat decorative | Flat decorative |
| Diameter across face of capitulum | 67 to 76 mm | 60 to 75 mm |
| Branching pattern | Spreading | Spreading |
| Nat. season flower date: | | |
| in Salinas, CA | Aug 14 to 27 | Aug 16 to 22 |
| in Hightstown, NJ | Sep 22 to 30 | Sep 20 to 30 |
| Plant height: | 28 to 33 cm | 25 to 28 cm |

What is claimed is:

1. A new and distinct Chrysanthemum plant named Empire Spotlight, as described and illustrated.

* * * * *

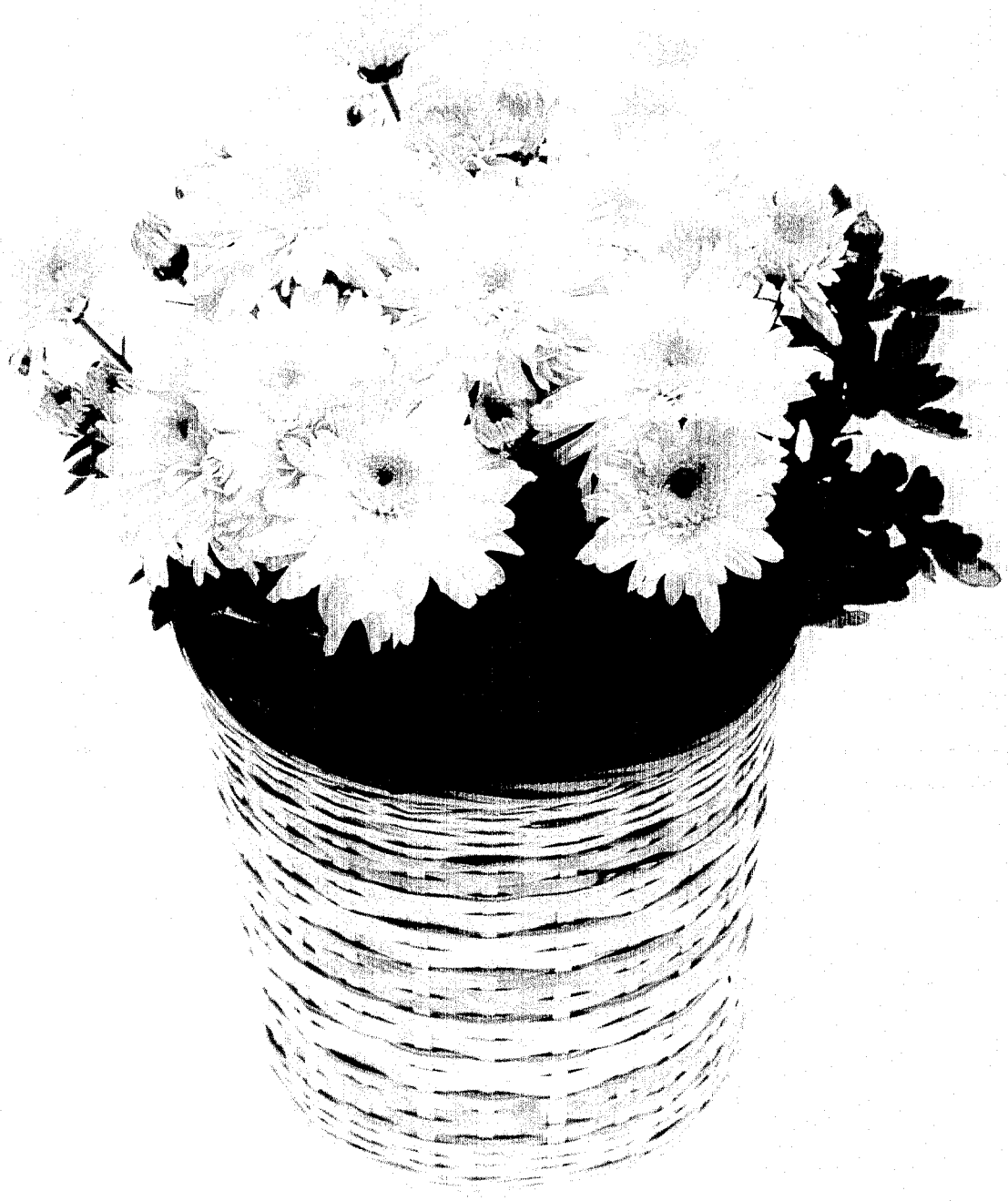

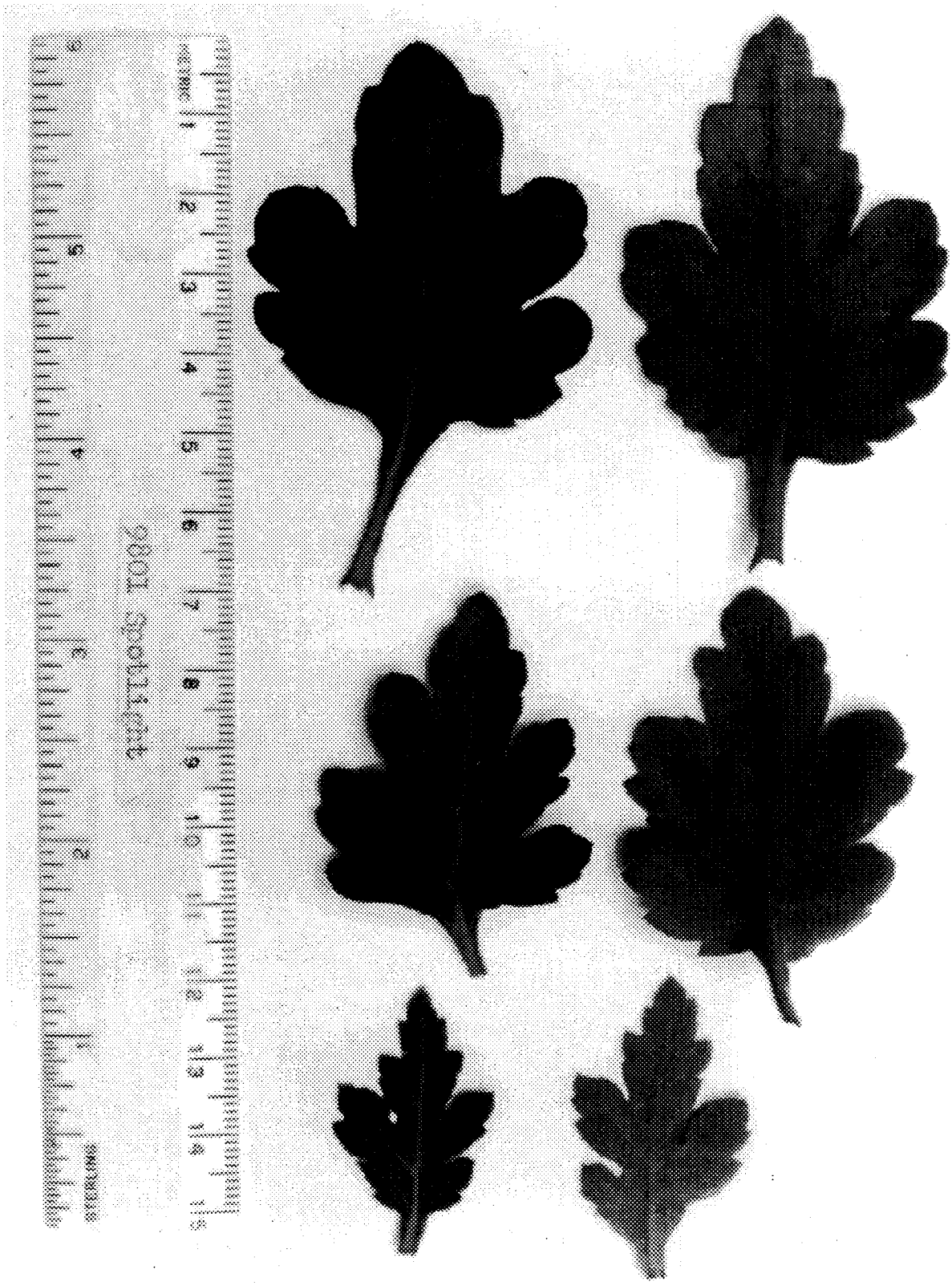
good Scientific Tools

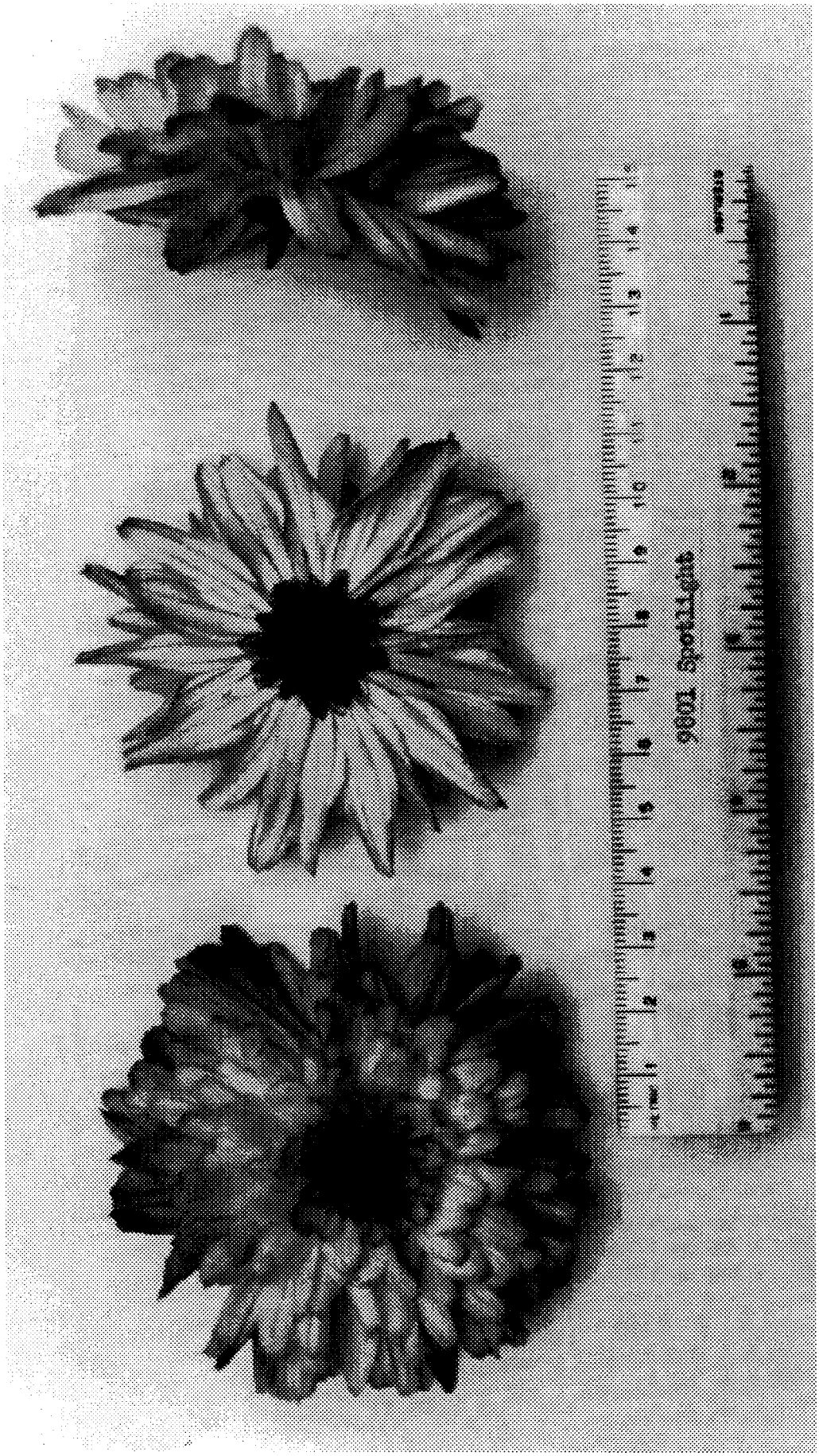
Specimen 1006